(12) United States Patent
Perry

(10) Patent No.: US 8,882,714 B1
(45) Date of Patent: Nov. 11, 2014

(54) NEEDLE WITH GATED STYLET

(76) Inventor: Robert J. Perry, Oklahoma City, OK (US)

(*) Notice: Subject to any disclaimer, the term of this patent is extended or adjusted under 35 U.S.C. 154(b) by 0 days.

(21) Appl. No.: 12/692,938

(22) Filed: Jan. 25, 2010

Related U.S. Application Data

(60) Provisional application No. 61/146,760, filed on Jan. 23, 2009.

(51) Int. Cl.
*A61M 5/178* (2006.01)

(52) U.S. Cl.
USPC .................................... 604/164.02

(58) Field of Classification Search
USPC ............ 604/164.01, 164.02, 167.01, 167.03, 604/167.05; 600/565–567
See application file for complete search history.

(56) References Cited

U.S. PATENT DOCUMENTS

| | | | |
|---|---|---|---|
| 3,413,970 A * | 12/1968 | Rockwell | 600/487 |
| 3,844,272 A * | 10/1974 | Banko | 600/566 |
| 4,143,853 A | 3/1979 | Abramson | |
| 4,297,081 A * | 10/1981 | Irvin | 417/2 |
| 4,299,705 A * | 11/1981 | Russell | 210/647 |
| 4,673,393 A | 6/1987 | Suzuki et al. | |
| 4,842,591 A | 6/1989 | Luther | |
| 4,895,565 A | 1/1990 | Hillstead | |
| 4,966,588 A | 10/1990 | Rayman et al. | |
| 5,012,818 A * | 5/1991 | Joishy | 600/567 |
| 5,085,645 A | 2/1992 | Purdy et al. | |
| 5,199,948 A | 4/1993 | McPhee | |
| 5,295,658 A | 3/1994 | Atkinson et al. | |
| 5,322,516 A | 6/1994 | Brugger | |
| 5,441,487 A | 8/1995 | Vedder | |
| 5,843,046 A | 12/1998 | Motisi et al. | |
| 5,848,966 A | 12/1998 | Gusakov et al. | |
| 6,755,391 B2 | 6/2004 | Newton et al. | |
| 6,840,501 B2 | 1/2005 | Doyle | |
| 7,766,878 B2 * | 8/2010 | Tremaglio et al. | 604/167.05 |
| 2002/0147431 A1 | 10/2002 | Lopez et al. | |
| 2003/0098430 A1 | 5/2003 | Leinsing et al. | |
| 2007/0203455 A1 * | 8/2007 | Tremaglio et al. | 604/164.01 |

* cited by examiner

*Primary Examiner* — Aarti B Berdichevsky
(74) *Attorney, Agent, or Firm* — San Diego IP Law Group LLP

(57) ABSTRACT

In accordance with preferred embodiments, a needle with gated stylet is provided that is useful for controlled fluid transfer with a patient's body. Preferably, the needle with gated stylet includes a hollow core needle providing a needle tip and at least two fluid transfer apertures with the stylet removably disposed within the needle. In an alternate embodiment, a needle providing a hollow core, an insertion tip, and a fluid transfer aperture adjacent the insertion tip and communicating with the hollow core, and a stylet disposed within the hollow core, cooperating with the fluid transfer aperture to preclude fluid flow through the fluid transfer aperture when the stylet is in a first position adjacent the insertion tip and promote fluid flow through the transfer aperture when the stylet is in a second position adjacent the insertion tip.

7 Claims, 3 Drawing Sheets

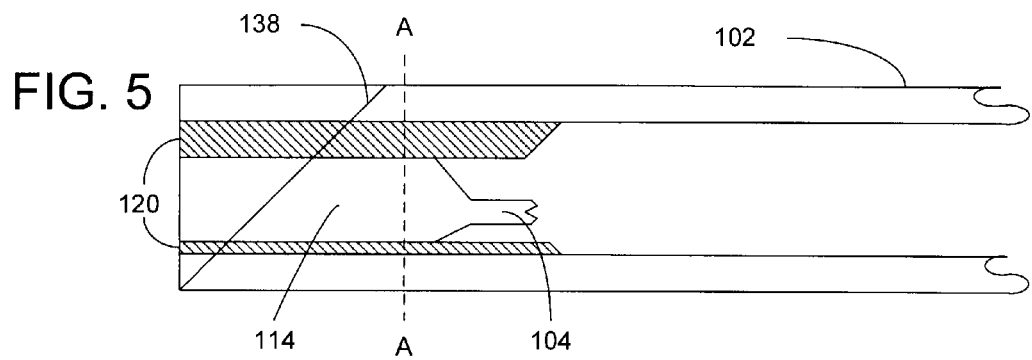
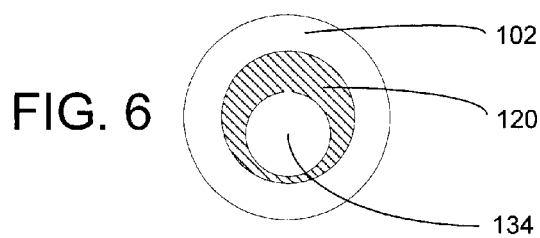
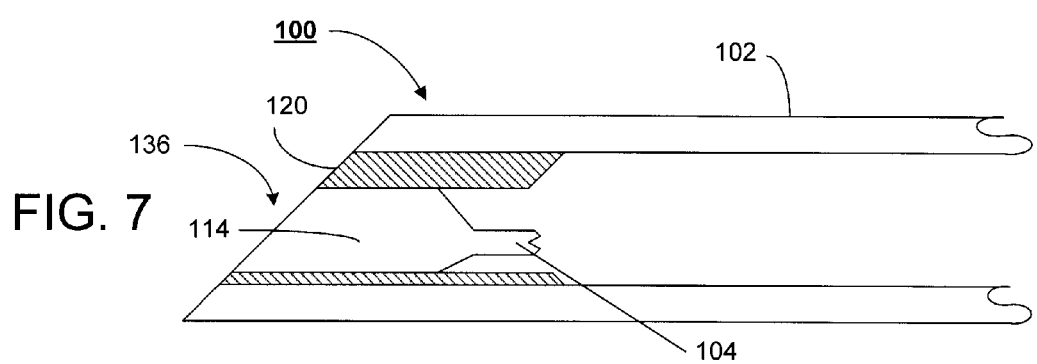
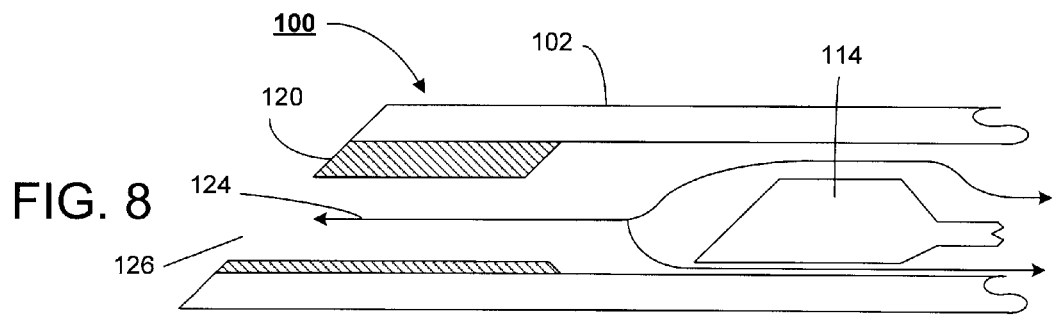

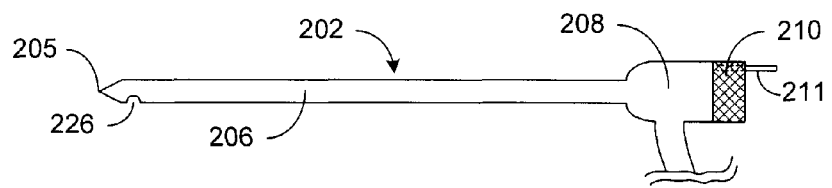
FIG. 9
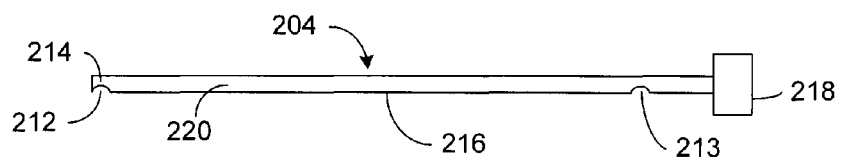
FIG. 10
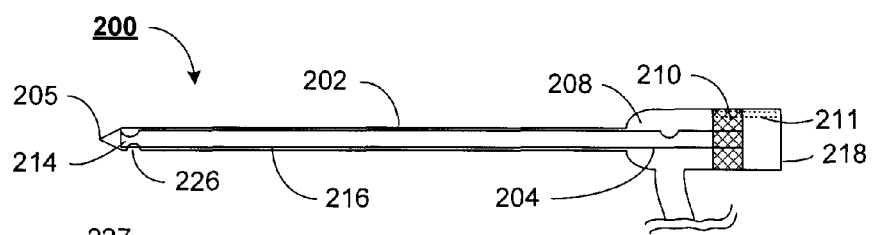
FIG. 11
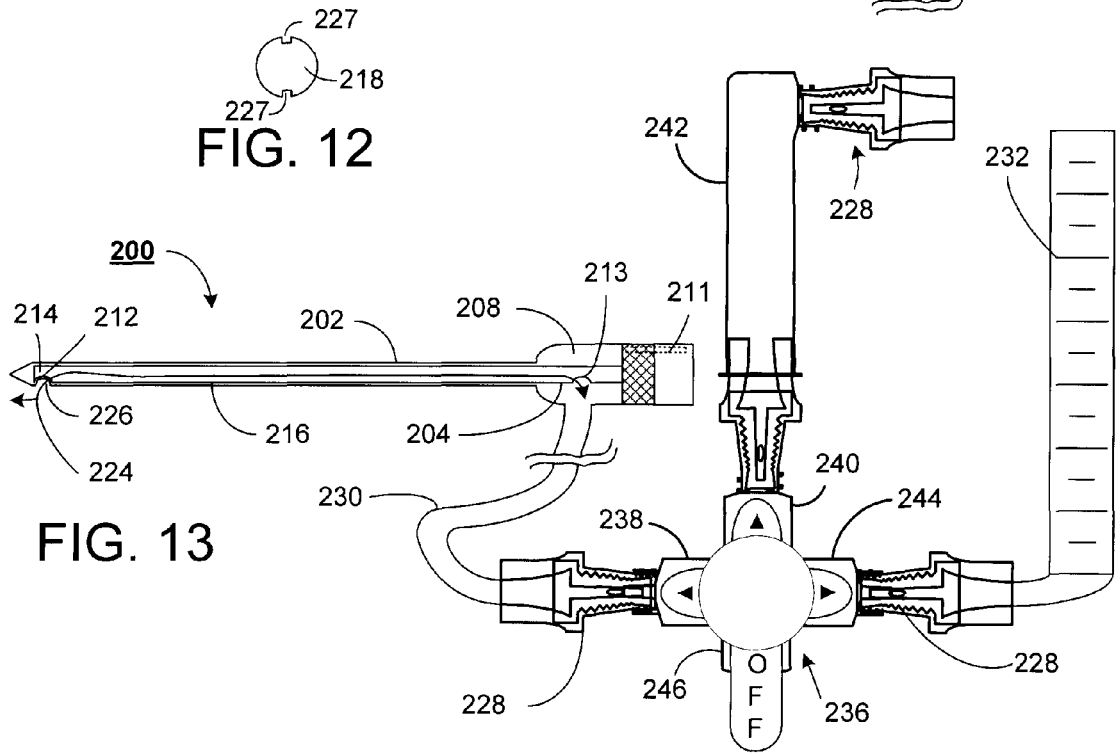
FIG. 12
FIG. 13

NEEDLE WITH GATED STYLET

RELATED APPLICATIONS

This application claims priority to U.S. Provisional Application No. 61/146,760 filed Jan. 23, 2009, entitled "Needle With Gated Stylet."

FIELD OF THE INVENTION

This invention relates to medical devices, and in particular, but not by way of limitation, to a medical procedure needle with gated stylet.

BACKGROUND

As the cost of healthcare continues to escalate, increased risks to health care providers from fluid born diseases mount, and a desire to reduce trauma experienced by patients undergoing medical procedures, the medical community is faced with an increasingly difficult environment in which to practice medicine.

An example of this increasingly difficult practice environment is spinal tap procedures. Although spinal taps are required to diagnose certain abnormalities and deliver therapeutic intervention, spinal tap procedures are time consuming, difficult and error prone.

Challenges remain and a need persists for improvements in methods and apparatuses for use in accommodating effective and efficient deployment and use of health care provider's time, medical procedure kits, and a reduction in the exposure of health care providers to medical hazards.

SUMMARY OF THE INVENTION

In accordance with preferred embodiments, a needle with gated stylet is provided that is useful to remove from or deliver fluid to a patient's body.

In a preferred embodiment, the needle with gated stylet includes a hollow core needle providing a needle tip and at least two fluid transfer apertures, and a stylet removably disposed in the needle, wherein at least a portion of said stylet is disposed between the fluid transfer apertures and adjacent the needle tip during an operative state of fluidic communication between said fluid transfer apertures.

In an alternate embodiment, a needle providing a hollow core, an insertion tip, and a fluid transfer aperture adjacent the insertion tip and communicating with the hollow core, and a stylet disposed within the hollow core, cooperating with the fluid transfer aperture to preclude fluid flow through the fluid transfer aperture when the stylet is in a first position adjacent the insertion tip and promote fluid flow through the transfer aperture when the stylet is in a second position adjacent the insertion tip.

These and various other features and advantages that characterize the claimed invention will be apparent upon reading the following detailed description and upon review of the associated drawings.

BRIEF DESCRIPTION OF THE DRAWINGS

FIG. 5 reveals a partial cutaway view in elevation of a needle tip of the present invention.

FIG. 6 shows a cross section view through A-A of the needle tip end manufacture of the inventive needle with gated stylet of FIG. 5.

FIG. 7 illustrates a partial cutaway view in elevation of the needle tip of FIG. 5.

FIG. 8 depicts a partial cutaway view in elevation of the needle tip of FIG. 5.

FIG. 9 portrays a view in elevation of a needle of the inventive needle with gated stylet.

FIG. 10 illustrates a view in elevation of a stylet of the inventive needle with gated stylet of FIG. 9.

FIG. 11 shows a partial cutaway view in elevation of the stylet disposed within the needle of FIG. 9.

FIG. 12 depicts an end view of the stylet providing keyways, which interface with keys provided by the needle of FIG. 9.

FIG. 13 reveals a partial cutaway view in elevation of the stylet disposed within the needle of FIG. 9.

DETAILED DESCRIPTION OF A PREFERRED EMBODIMENT

Detailed descriptions of the preferred embodiments are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
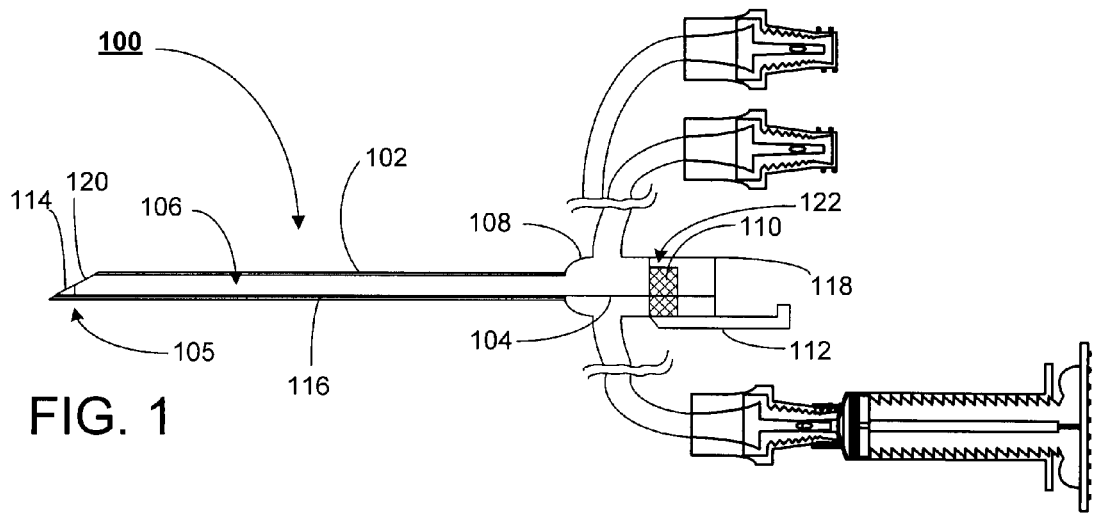
FIG. 1 shows a partial cutaway view in elevation of an inventive needle with gated stylet of the present invention.

Reference will now be made in detail to one or more examples of preferred embodiments of the invention depicted in the figures. Each example is provided by way of explanation of the invention, and not meant as a limitation of the invention. FIG. 1 shows a preferred embodiment of an inventive medical procedure kit (IMPK) 100 that preferably includes a needle 102 and stylet 104. The needle 102 preferably provides a needle tip 105 at its distal end, a fluid reservoir 108 at its proximal end, a hollow core 106 disposed between the needle tip 105 and the fluid reservoir 108, a diaphragm 110 adjacent the fluid reservoir 108, and a stylet support shelf 112 communicating with the fluid reservoir 108 and adjacent the diaphragm 110.

The stylet 104 preferably provides a plug portion 114 at its distal end, a cap portion 118 at its proximal end, and a body portion 116 disposed between the plug portion 114 and the cap portion 118. The body portion 116 preferably passes through the diaphragm 110 to maintain continuity with the cap portion 118, while the diaphragm 110 prevents fluid leakage from the fluid reservoir 108.

When the stylet 104 is disposed within the needle 102, the plug portion 114 of the stylet 104 may reversibly engage the insert 120 of the needle 102 in a preclude fluid flow position, as shown in FIG. 1. A key 122 located at the side of the cap portion 118 helps orient the stylet 104 for reversible engagement with the diaphragm 110; and therefore helps orient the plug portion 114 for reversible engagement with the insert 120.

With the preferred embodiment in the preclude fluid flow position, as shown in FIG. 1, the operator positions the IMPK 100 in the desired location by driving the needle tip 105 through the patient's body. In a preferred embodiment, the IMPK 100 will be inserted in the lumbosacral spine (low back) and advanced through multiple layers of tissue until the IMPK 100 pierces the dura and enters the cerebrospinal fluid.

Figure 2:
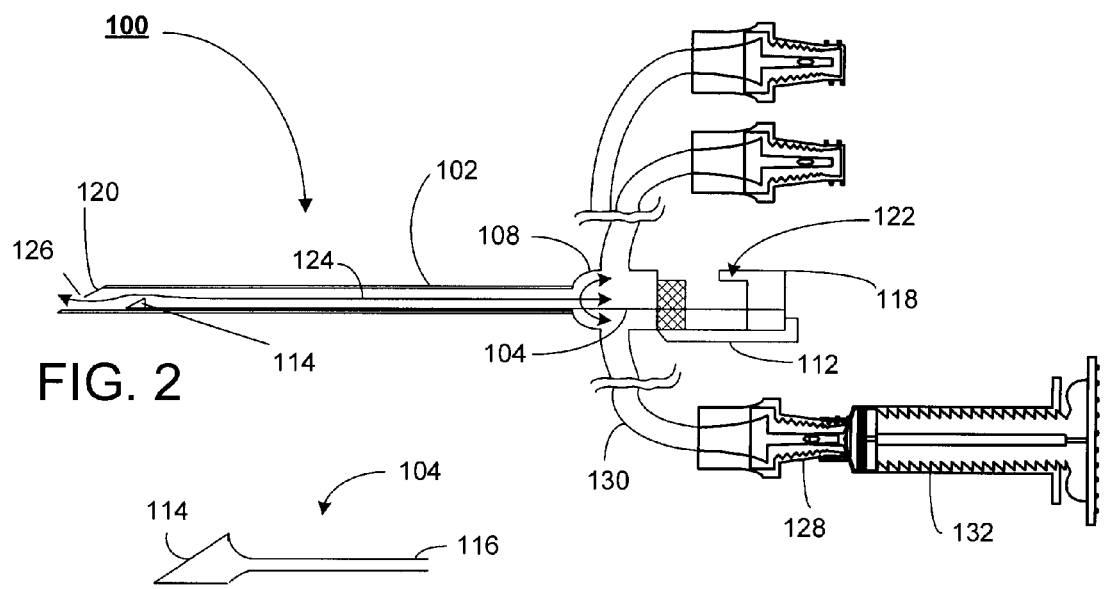
FIG. 2 portrays a partial cutaway view in elevation in promote fluid flow position of the inventive needle with gated stylet of FIG. 1.

FIG. 2 illustrates the IMPK 100 repositioned by the operator with the plug portion 114 of the stylet 104 adjacent the insert 120 of the needle 102 to promote fluid flow 124 through an aperture 126. During the repositioning operation, the cap portion 118 of the stylet 104 communicates with the stylet support shelf 112 that provides structural support to the IMPK 100 by limiting motion of the stylet 104 off axis, which is defined by the distal and proximal ends of the stylet 104.

As shown in FIG. 2, the fluid reservoir 108 of the needle 102 is coupled to a fluid valve 128 by a tubing 130 disposed between the fluid reservoir 108 and the fluid valve 128. Various medical devices, such as a syringe 132, may reversibly engage the fluid valve 128. The operator may remove fluid from the fluid reservoir 108 and deliver fluid to the fluid reservoir 108 through the fluid valve 128 and the tubing 130; hence, fluid may be removed from and delivered to the patient.

Figure 3:
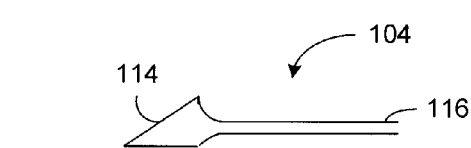
FIG. 3 illustrates a close up view in an elevation of a plug portion of the inventive needle with gated stylet of FIG. 1.
Figure 4:
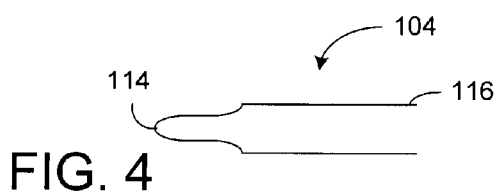
FIG. 4 depicts a close up view from the top of the plug portion of the inventive needle with gated stylet of FIG. 1.

FIG. 3 shows close up in an elevation of the plug portion 114 adjacent the body portion 116 at the distal end of the stylet 104, while FIG. 4 shows close up from top of the plug portion 114 adjacent the body portion 116 at the distal end of the stylet 104. The plug portion 114 can take various shapes for reversible engagement with the insert 120 of the needle 102: circular, triangular, hexagonal, or any other effective shape.

FIG. 5 shows the needle 102, an insert 120 at the distal end of needle 102, and the plug portion 114 of the stylet 104 reversibly engaging the insert 120. The insert 120 is preferably attached to the needle 102 by adhesive, weld, or other joining procedure. Alternatively, the insert 120 may be made of one piece with the needle 102. In a preferred embodiment, the insert 120 has an offset center bore 134 as best seen in FIG. 6 cross section.

A bevel 136 of the IMPK 100, shown in FIG. 7, is produced by cutting along line 138 with, as shown in FIG. 5, or without, as not shown, the stylet 104 disposed within the needle 102 and its insert 120. FIG. 7 shows the IMPK 100 after the bevel 136 is made with the plug portion 114 of the stylet 104 reversibly engaging the insert 120 of the needle 102 in the preclude fluid flow position. By contrast, FIG. 8 shows the IMPK 100 repositioned by the operator with the plug portion 114 adjacent the insert 120 of the needle 102 to promote fluid flow 124 through the aperture 126.

In an alternate preferred embodiment, FIG. 9 shows a needle 202 that preferably provides an insertion tip 205 at its distal end, a fluid reservoir 208 at its proximal end, a hollow core 206 disposed between the insertion tip 205 and the fluid reservoir 208, a diaphragm 210 adjacent the fluid reservoir 208, and a key 211 supported by the fluid reservoir 208 and extending through the diaphragm 210.

As further shown in FIG. 10, this alternate preferred embodiment includes a stylet 204 that provides a plug portion 214 at its distal end, a cap portion 218 at its proximal end, and a body portion 216 disposed between the plug portion 214 and the cap portion 218. The stylet 204 further provides a distal aperture 212 at its distal end and a proximal aperture 213 at its proximal end, and a hollow core 220 disposed between the distal aperture 212 and the proximal aperture 213. In FIG. 10, the distal aperture 212 is shown on the side of the stylet 204, but distal aperture 212 could appear on the end or at any other suitable location on the stylet 204, in keeping with the current embodiment.

FIG. 11 shows the IMPK 200 that preferably includes the needle 202 and the stylet 204. When the stylet 204 is disposed within the needle 202, the plug portion 214 of the stylet 204 may reversibly engage the aperture 226 of the needle 202 in preclude fluid flow position, as shown in FIG. 11. In addition, the body portion 216 of the stylet 204 preferably passes through the diaphragm 210 to maintain continuity with the cap portion 218 of the stylet 204, while the diaphragm 210 prevents fluid leakage from the fluid reservoir 208. The key 211 interacts with the keyways 227, of FIG. 12, provided by the cap portion 218 to orient the stylet 204 for reversible engagement with the diaphragm 210; and therefore helps orient the plug portion 214 for reversible engagement with the aperture 226.

With the preferred embodiment in the preclude fluid flow position, as shown in FIG. 11, the operator positions the IMPK 200 in the desired location by driving the insertion tip 205 through the patient's body. Most typically, the IMPK 200 will be inserted in the lumbosacral spine (low back) and advanced through multiple layers of tissue until the IMPK 200 pierces the dura and enters the cerebrospinal fluid.

FIG. 13 illustrates the IMPK 200 repositioned by the operator with the plug portion 214 of the stylet 204 adjacent the aperture 226 of the needle 202 to promote fluid flow 224 through the aperture 226 and the distal aperture 212 of the stylet 204. Fluid communicates from the body portion 216 of the stylet 204 through the proximal aperture 213 of the stylet 204 with the fluid reservoir 208 of needle 202. This fluid reservoir 208 is coupled to a fluid valve 228 by a tubing 230 disposed between the fluid reservoir 208 and the fluid valve 228. Various medical devices, such as a manometer 232, may reversibly engage the fluid valve 228, which in this case is affixed to a three-way stopcock 236. The three-way stopcock 236 allows the operator to occlude fluid flow 224 after fluid valve 228 is accessed and to thereby direct fluid between various medical devices. The operator may remove fluid from the fluid reservoir 208 and deliver fluid to the fluid reservoir 208 through the fluid valve 228 and the tubing 230; hence, fluid may be removed from and delivered to the patient.

In a preferred embodiment shown by FIG. 13, the three-way stopcock 236 includes: a first fluid flow position 238, which promotes fluid flow from the fluid reservoir 208 to the monometer 232; a second fluid flow position 240, which promotes fluid flow from the fluid reservoir 208 to a fluid tube 242; a third fluid flow position 244, which promotes fluid flow from the fluid tube 242 to the monometer 232; and a fourth fluid flow position 246, which is an off position that precludes fluid flow through the stopcock 236.

Preferably, the second flow position 240 of the three-way stopcock 236 is operative only when the fluid tube 242 is engaged with the second flow position 240 of the three-way stopcock 236, and the preferably the fluid tube 240 is configured with a fluid valve 228 which selectively opens to atmosphere or to vacuum. Further, in a preferred embodiment the first and second flow positions 238 and 244 respectfully, are operative only when their corresponding tubing 230 and monometer 232 is engaged and interacting therewith.

The needles (102, 202) are preferably made from stainless steel and are preferably thin-walled 18 gauge, 20 gauge, 22 gauge, 25 gauge, or other size suitable for the intended use of the needles (102, 202). The fluid reservoirs (108, 208) are preferably made from hard polymer, and the fluid reservoirs (108, 208) are preferably translucent so that fluid in the fluid reservoirs (108, 208) can be viewed by the operator. The diaphragms (110, 210) are preferably made from pliable polymer. The stylet support shelf 112 is preferably made from hard polymer. The needles (102, 202) of FIG. 1 and FIG. 9 are not limiting and may be made from other suitable materials known to one skilled in the art.

The plug portions (114, 214) and body portions (116, 216) are preferably made from stainless steel. The plug portion 114 and body portion 116 of stylet 104 are preferably formed by coining; however, they may be formed by casting, forging, or other suitable manufacture known to one skilled in the art. The plug portion 114 is sized to reversibly engage the insert 120 to preclude fluid flow, while the plug portion 214 is sized to reversibly engage the aperture 226 to preclude fluid flow. The cap portions (118, 218) are preferably made from hard polymer. The stylets (104, 204) of FIG. 1 and FIG. 9 are not limiting and may be made from other suitable materials known to one skilled in the art.

The tubings (130, 230) are preferably made from flexible polymer, although other suitable materials known to one skilled in the art may be used.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. An apparatus comprising:
    a needle providing a hollow core, an insertion tip interacting with the hollow core, and a fluid transfer aperture adjacent to said insertion tip, said aperture in fluidic communication with said hollow core, wherein the insertion tip is a portion of the needle, wherein the insertion tip is a pointed, flesh-piercing tip of the needle, said insertion tip of the needle is the first structural portion of the apparatus to engage a patient's tissue when the apparatus is inserted into the tissue of the patient, wherein the needle comprises a fluid reservoir as part of the needle; and
    a stylet disposed within the hollow core, cooperating with said fluid transfer aperture to preclude fluid flow through said fluid transfer aperture when said stylet is in a first position, and to promote fluid flow through said transfer aperture when the stylet is in a second position adjacent the insertion tip, wherein the stylet and the needle are two separate components,
    wherein the stylet comprises a plug portion at its distal end, a cap portion at its proximal end, and a hollow cylindrical body portion disposed between the plug portion and the cap portion, wherein said plug portion precludes fluid flow through said fluid transfer aperture when said stylet is in the first position, and said plug portion promotes fluid flow through said transfer aperture when the stylet is in the second position adjacent said insertion tip, and further
    wherein the hollow cylindrical body portion comprises a first fluid transfer aperture, and a second fluid transfer aperture, the first fluid transfer aperture and second fluid transfer aperture being disposed through an outer surface of the hollow cylindrical body portion, and the first fluid transfer aperture of the stylet is adjacent to said insertion tip and the second fluid transfer aperture of the stylet is adjacent to said cap portion, wherein the stylet is removably disposed in the needle.

2. The apparatus of claim 1, wherein said fluid reservoir is in communication with at least one of the first or second fluid transfer apertures of the stylet, which are different and distinct from the fluid transfer aperture adjacent said insertion tip.

3. The apparatus of claim 2, in which a fluid is present in said fluid reservoir, the fluid is responsive to a fluid valve coupled to said fluid reservoir.

4. The apparatus of claim 3, further comprising a three-way valve in fluidic communication with said fluid reservoir, when said three-way valve is operatively coupled with said fluid reservoir.

5. The apparatus of claim 4, further comprising a manometer in fluidic communication with said fluid reservoir, when said three-way valve is operatively coupled with said manometer and said three-way valve is positioned for a fluidic interaction between said fluid reservoir and said manometer.

6. The apparatus of claim 5, further comprising a fluid tube in fluidic communication with said fluid reservoir, when said three-way valve is operatively coupled with said fluid tube and said three-way valve is positioned for a fluidic interaction between said fluid reservoir and said fluid tube.

7. The apparatus of claim 6, in which said fluid tube and said manometer are in fluidic communication with each other, when said three-way valve is operatively coupled with said fluid tube and said three-way valve is positioned for a fluidic interaction between said fluid manometer and said fluid tube.

* * * * *